United States Patent [19]

Cabri et al.

[11] Patent Number: 5,103,029
[45] Date of Patent: Apr. 7, 1992

[54] PROCESS FOR PREPARING 4-DEMETHOXYDAUNOMYCINONE

[75] Inventors: Walter Cabri, Limbiate; Silvia de Bernardinis, Milan; Franco Francalanci, Novara; Sergio Penco, Milan, all of Italy

[73] Assignee: Farmitalia Carlo Erba S.r.l., Milan, Italy

[21] Appl. No.: 333,951

[22] Filed: Apr. 6, 1989

[30] Foreign Application Priority Data

Apr. 11, 1988 [GB] United Kingdom ............... 8808475

[51] Int. Cl.$^5$ .................................. C07C 103/26
[52] U.S. Cl. ..................... 552/207; 552/201
[58] Field of Search ............. 552/206, 201, 207

[56] References Cited

U.S. PATENT DOCUMENTS

| | | | |
|---|---|---|---|
| 4,012,784 | 3/1977 | Marco et al. | 435/78 |
| 4,020,270 | 4/1977 | Arcamone et al. | 552/201 |
| 4,046,878 | 9/1977 | Patelli et al. | 536/17 |
| 4,097,988 | 7/1978 | Hauschild | 29/620 |
| 4,132,721 | 1/1979 | Bernardi et al. | 552/206 |
| 4,348,388 | 9/1982 | Garland et al. | 552/201 |
| 4,495,103 | 1/1985 | Terashima et al. | 552/206 |

FOREIGN PATENT DOCUMENTS

| | | | |
|---|---|---|---|
| 0337665 | 10/1989 | European Pat. Off. | 552/201 |
| 2274629 | 1/1976 | France . | |

OTHER PUBLICATIONS

Tetrahedron Letters, vol. 27, No. 45, 1986, pp. 5541-5544, Pergamon Journals Ltd, GB; S. Cacchi et al.: "Palladium-Catalyzed Triethylammonium Formate Reduction of Aryl Triflates. A Selective Method for the Deoxygenation of Phenols".
Canadian Journal of Chemistry, vol. 49, No. 15, Aug. 1, 71, pp. 2712-2718, The National Research Council of Canada; C. M. Wong et al.: "Synthetic Studies of Hydronaphthacenic Antibiotics. I. The Synthesis of 4-Demethoxy-7-O-Methyl Daunomycinone".
Barnett, *Anthracene and Anthraquinone*, 1921, pp. 261, 266.

*Primary Examiner*—C. Warren Ivy
*Assistant Examiner*—Raymond Covington
*Attorney, Agent, or Firm*—Oblon, Spivak, McClelland, Maier & Neustadt

[57] ABSTRACT

4-Demethoxy-daunomycinone I:

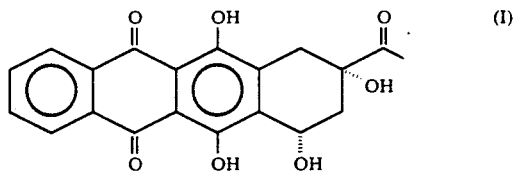

the known aglycone of 4-demethoxy-daunorubicin, is prepared by protecting the 13-keto group of 4-demethyldaunomycinone, sulfonylating the 4-hydroxy group, reacting the sulfonylated compound, in an appropriate reducing environment, with a catalytic amount of a transition metal complex, preferably palladium or nickel with 1,3 diphenylphosphinopropane or 1,1'-bis (diphenylphosphino) ferrocene, and eliminating the 13-dioxolanyl group by treatment with trifluoroacetic acid.

1 Claim, No Drawings

PROCESS FOR PREPARING 4-DEMETHOXYDAUNOMYCINONE

The present invention relates to an improved process for preparing 4-demethoxydaunomycinone which has the formula I:

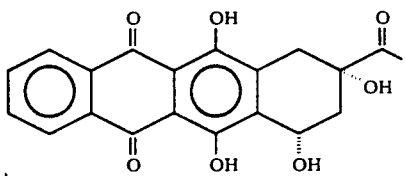

In the British Patent Application No. 8803301, by the same Applicant, a novel process for preparing 4-demethoxydaunomycinone has been described. The process of that invention was different from the prior art in that it started from the natural daunomycinone, was faster, more efficient and gave the final product in much higher yield than previous processes. Moreover it did not require an optical resolution step.

The process for the preparation of 4-demethoxydaunomycinone according to the previous invention used as the starting material (+)daunomycinone which may be obtained according the procedure described in U.S. Pat. No. 4,012,284. The (+)daunomycinone was demethylated by treatment with $AlCl_3$ to give 4-demethyldaunomycinone and transformed into its 13-dioxolanyl derivative (3) by reaction with ethylene glycol. The obtained compound (3), 4-demethyl-13-dioxolanyl-daunomycinone, was sulfonated in position C4-OH without any protection of the remaining OH groups. The sulfonating agent was a sulfonyl chloride of formula (II)

$$R-SO_2Cl \qquad (II)$$

wherein R was, preferably, a 4-fluorophenyl or 4-tolyl group.

The sulfonylated compound was subsequently treated with, preferably, 4-methoxybenzylamine or 3,4-dimethyoxybenzylamine. The obtained 4-amino derivative was diazotised, typically in an acidic environment with sodium nitrite. The so formed diazonium salt was finally reduced under mild conditions, for example with 50% hypophosphorous acid, to give 4-demethoxydaunomycinone.

According to the present invention, there is provided a process for the preparation of 4-demethoxydaunomycinone of formula (I), which process comprises (i) reacting 4-demethyl-13-dioxolanyldaunomycinone of formula (3):

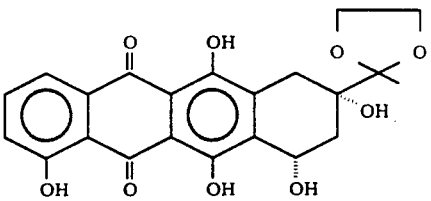

in the presence of N,N-diisopropylethylamine and a catalytic amount of 4-dimethylamino-pyridine, with a sulfonyl compound of formula II:

$$R-SO_2X \qquad (II)$$

wherein X represents a halogen atom, a $OSO_2R$ group, an imidazolyl group, a $NH(C_6H_5)(RSO_2)$ group or another group capable of reacting with a phenol to give a sulfonate and R represents an alkyl group having from 1 to 10 carbon atoms optionally substituted by one or more halogen atoms or an aryl group optionally substituted by halogen, alkyl, alkoxy or nitro;

(ii) reacting the resultant sulfonated 4-demethyl-13-dioxolanyl-daunomycinone of formula (4):

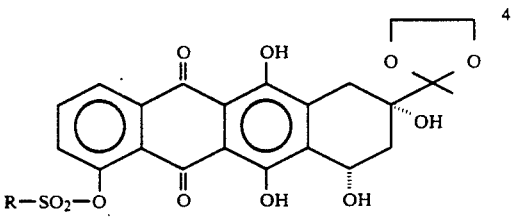

wherein R is as defined above, in a reducing environment with a catalytic amount of a compound of formula $$ML_nL'_m \qquad (III)$$

wherein M represents a transition metal atom, L and L', which may be the same or different, each represent an anion or a neutral molecule, and n and m may vary from 0 to 4; and (iii) removing the 13-oxo protecting group from the resultant dioxolanyl-daunomycinone (5):

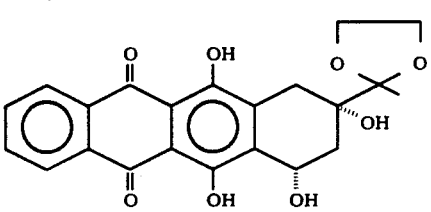

The improved process is shown in the following Scheme:

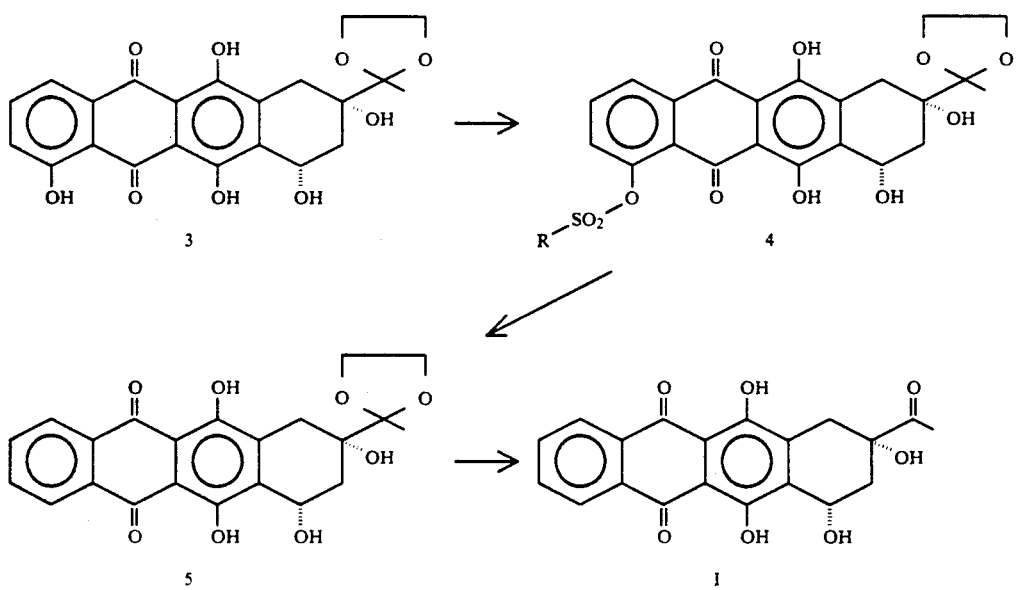

The intermediate 13-dioxolanyl derivative (3) can be prepared from 4-demethyldaunomycinone which is also called carminomycinone. This may be achieved by treatment with ethylene glycol, for example in the presence of p-toluenesulfonic acid at the reflux temperature. 4-Demethyldaunomycinone can in turn be prepared from (+)daunomycinone. Demethylation can be effected by treatment with $AlCl_3$, typically in an inert organic solvent such as nitrobenzene at the reflux temperature. Such a process is described in U.S. Pat. No. 4,188,377.

In step (i), the 4-demethyl-13-dioxolanyldaunomycinone (3) is reacted with a sulfonylating agent of formula (II):

$$R-SO_2-X$$

wherein X may be a halogen atom, a $OSO_2R$ group, an imidazolyl group, a $NH(C_6H_5)(RSO_2)$ group or another group capable of reacting with a phenol to give a sulfonate and R represents an alkyl group having from 1 to 10 carbon atoms optionally substituted by one or more halogen atoms or an aryl group optionally substituted by halogen, alkyl, alkoxy or nitro to obtain the 4-sulfonylated 13-dioxolanyl compound (4). Preferred groups which R may represent are trifluoromethanesulfonyl, 4-fluorophenyl and 4-tolyl. Reaction may be effected with the 4-demethyl-13-dioxolanyldaunomycinone, dissolved in pyridine, at room temperature.

The sulfonated 4-demethyl-13-dioxolanyl-daunomycinone (4) is transformed into the final product (I) in two steps, which can be effected without isolating the intervening intermediate, with improved yields and purity. In step (ii) the sulfonated compound (4) is treated in an appropriate reducing environment with a compound of formula (II) (hereunder referred to as catalyst):

$$ML_nL'_m \qquad (III)$$

wherein M represents a transition metal atom; L and L', which may be the same or different, may be an anion such as $Cl^-$ or $CH_3COO^-$ or a neutral molecule such as a solvent molecule, a mono- or a di-phosphine, a phosphite or a diamine; and n and m may vary from 0 to 4. Typically m+n is at least 1, for example 1, 2, 3 or 4. Preferred transition metal atoms which M may represent are palladium and nickel. Preferred group which L and/or L' may represent are chelating diphosphines such as 1,3-diphenylphosphinopropane or 1,1'-bis(diphenylphosphino)ferrocene. The sulfonated compound (4) is therefore treated with a catalytic amount of a transition metal complex, preferably one between a transition metal atom such as palladium or nickel and a chelating ligand as above such as 1,3-diphenylphosphinopropane or 1,1'-bis(diphenylphosphino)ferrocene. The molar ratio of transition metal atom: chelating ligand is generally from 1:1 to 1:4.

As an example of how step (ii) may be effected, the sulfonated compound (4) is dissolved in an appropriate polar solvent and added, under an inert atmosphere, to a solution of catalyst either preformed or generated "in situ" from suitable precursors, in the presence of a reducing system which is able to act as a formal hydrogen donor. A suitable reducing system under the conditions of the invention is a trialkylammonium formate, formed "in situ" by addition of formic acid and a trialkylamine. The temperature of the reaction is typically from 0° to 150° C., preferably from 30° to 100° C. Reaction may be effected for from 4 to 24 hours, preferably from 6 to 18 hours. The catalyst is used in a molar ratio to the sulfonated compound (4) of from 1:1 to 1:10000, preferably between 1:20 and 1:1000.

The reduction step [(4) to (5)] has recently been applied to simple molecules such as naphthalene and anthracene derivatives (Tetrahedron Lett. 27 (1986) 5541; ibidem 28 (1987) 1381). However, it has never been used for the hydrogenolysis of sulfonates of variously substituted anthraquinone molecules. In particular the reaction is new in anthracycline chemistry, probably because of the presence of other interferring functional groups. The problems arising from the presence of said groups, namely aromatization of ring A, formation of 7-deoxy derivatives, hydrolysis of 4-sulfonyl derivative and/or modifications of the quinone moiety can be suppressed under the conditions of the invention.

In step (iii) the 13-oxo protecting group is removed from the resultant 4-demethoxy-13-dioxolanyl-daunomycinone (5). This may be achieved with trifluoroacetic acid without isolation of compound (5). For example, 4-demethoxy-13-dioxolanyl-daunomycinone (5) can be treated with trifluoroacetic acid at room temperature for 1 hour. This gives the desired 4-demethoxy-daunomycinone (I). This can be purified by chromatography on silica gel using, as the eluent system, chloroform/acetone (9/1 by volume).

4-Demethoxy-daunomycinone is the aglycone moiety of the useful antitumor drug 4-demethoxy-daunorubicin. Accordingly, the present invention provides also a process for preparing 4-demethoxy-daunorubicin of formula (IV):

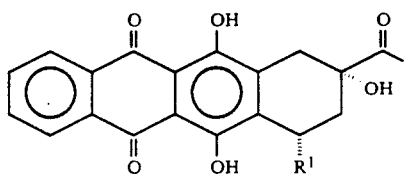

wherein $R^1$ represents

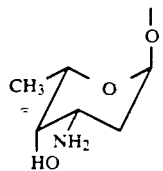

or a pharmaceutically acceptable salt thereof, which process comprises reacting 4-demethoxy-daunomycinone of formula (I) which has been prepared by a process according to the invention with an appropriate sugar derivative and, if desired, converting the 4-demethoxy-daunorubicin thus-obtained into a pharmaceutically acceptable salt thereof.

Preferably, the sugar derivative has the formula (V):

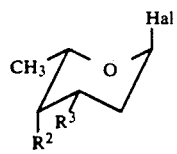

wherein Hal represents a halogen atom, $R^2$ represents a protected hydroxy group and $R^3$ represents a protected amino group, and the protecting groups are removed after reaction with the 4-demethoxy-daunomycinone. Preferably Hal is a chlorine atom. The hydroxy group may be protected by a trifluoroacetyl group. The amino group may be protected by a trifluoroacetyl group also.

The resulting 4-demethoxy-daunorubicin or pharmaceutically acceptable salt thereof may be formulated, for example for use as an antibiotic or as an antitumor agent, as a pharmaceutical composition also comprising a pharmaceutically acceptable carrier or diluent.

The following Examples illustreate the invention.

EXAMPLE 1:

4-Demethyl-4-trifluoromethansulfonyl-13-dioxolanyl-daunomycinone (4)

To a solution in pyridine (1.1 l) of 11 g (25.7 mmol) of (3), 22 ml (128.5 mmol) of diisopropylethylamine and 3.8 g (25.7 mmol) of 4-dimethylaminopyridine, cooled at 0° C., 12.7 ml (75.5 mmol) of trifluoromethanesulfonyl anhydride were added and the reaction mixture was stirred for 1 hour at room temperature. The reaction mixture was then cooled at 0° C. and 5 l of methylene chloride and 3 l of 10% hydrochloric acid added. After separation the organic phase was washed with water, dried over sodium sulfate and the solvent evaporated under reduced presure to leave 13.75 g of solid which was refluxed for 15 minutes in ethanol (350 ml) and filtered obtaining 8.25 g of (4). (HPLC : 91%)

HPLC analysis

Column: MERCK RP 18/7 μm (250×4.2 mm),

| Mobile phase: | | |
|---|---|---|
| A | 0.01 M sodium heptansulfonate/0.02 M phosphoric acid | 6 |
| | Acetonitrile | 4 |
| B | Methanol | 7 |
| | Acetonitrile | 3 |

Gradient: from 20% B to 70% in 25 min,
Flow rate: 1.5 ml/min,
Detector: UV at 254 nm.

$^1$H-NMR 300 MHz (in COCl$_3$):=1.47 (3H, s), 1.98 (1H, dd, J)=4.7, 14.6 Hz), 2.47 (1H, d, J=14.5 Hz), 2.79 (1H, d, J=19.0 Hz), 3.21 (2H, m), 3.82 (1H, bs); 4.09 (4H, s). 5.27 (1H, bs), 7.63 (1H, d, J=8.1 Hz), 7.88 (1H, t,J=7.9 hz), 8.48 (1H, d J=7.7 Hz), 13.26 (1H, s), 13.48 (1H, s).

M.S: m/z=560 (M+, base peak).

TLC on Kieselgel plate F 254 (Merck) using Chloroform/Acetone (8:2 by volume) Rf=0.56

EXAMPLE 2

4-Demethoxydaunomycinone (I)

To a solution of 10 g of (4) 17.8 mmol) in 250 ml of dimethylformamide under an inert atmostphere were successively added 10 ml of triethylamine, 2.7 ml of formic acid, 55 mg of 1,1'-bis-(diphenylphosphino) ferrocene (0.089 mmol) and 20 mg of palladium acetate (0.089 mmol). The reaction mixture was stirred for 7 hours at 40° C., then cooled to 0° C., acidified with 10% hydrochloric acid and extracted with methylene chloride. The organic phase was evaporated to dryness and the residue treated with 50 ml of trifluoroacetic acid for one hour at-room temperature. The reaction mixture was then diluted with 500 ml of water and extracted with methylene chloride. The organic layer was washed with saturated sodium bicarbonate and water till neutrality, dried over sodium sulfate and evaporated to dryness. The residue was chromatographated on silica gel (chloroform/acetone 9:1 by volume as eluant) obtaining 4.7 g (71.6%) of 4-demethoxydaunomycinone (I) (HPLC 98%).

$^1$H-NMR 300 MHz (in COCl$_3$):=2.19 (1H, dd, J=4.8,14.5 Hz), 2.37 (1H, ddd, J=2.0, 2.0, 14.5 Hz), 2.43 (3H, s), 2.95 (1H, d, J=18.6), 3.20 (1H, dd, J=2.0, 18.6 Hz), 3.83 (1H, d, J=4.8 Hz), 4.55 (1H, s), 5.32 (1H, ddd, J=2.0, 4.8, 4.8 Hz), 7.84–7.86 (2H, m), 8.33–8.36 (2H, m), 13.30 (1H, s), 13.60 (1H, s).

U.V. spectrum (in EtOH):=208, 252, 257, 285, 480, 500, 514 nm., λmax=252 nm.

I.R. spectrum (KBr pellet)=3450, 1715, 1625, 1585 cm$^{-1}$ [α]$^{20}$$_D$(C=0.1 in dioxane)= +159°

M.S.: m/z=368 (M$^+$, base peak)

TLC on Kieselgel plate F 254 (Merck) using chloroform/acetone (8:2 by volume) Rf=0.70

EXAMPLE 3

The reaction was carried out as described in example 2 except that dioxane (250 ml) was used as solvent an d1.3 diphenyl phosphinopropane (37 mg. 0.089 mmol) as ligand for palladium. After 16 hours at 60° C. the reaction mixture was worked up as described in example 2 obtaining 3.8 g (58% of (I)) (HPLC 97.6%).

EXAMPLE 4

The reaction was carried out as described in example 2 except that 200 mg of palladium acetate (0.89 mmol) and 560 mg of 1,2-bis [N-(1 phenylethyl), N-(diphenylphosphino) amino] ethane were used. After 14 hours at 60° C. the reaction mixture was worked up as described in example 2 obtaining 4.1 g (62.4%) of (I), (HPLC 98.3%).

I claim:

1. A process for the preparation of 4-demethoxydaunomycinone of formula (I):

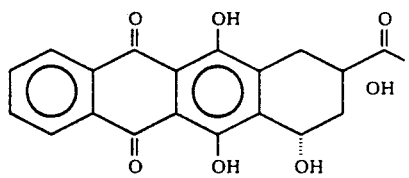
(I)

which process comprises
(i) reacting 4-demethyl-13-dioxolanyl-daunomycinone of formula (3):

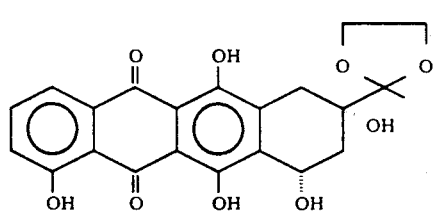
3 in the presence of N,N-diisopropylethylamine and a catalytic amount of 4-dimethylamino-pyridine, with a sulfonyl compound of formula II:

$$R-SO_2X \qquad (II)$$

wherein X represents a halogen atom, a OSO$_2$R group, an imidazolyl group, a NH(C$_6$H$_5$)(RSO$_2$) group or another group capable of reacting with a phenol to give a sulfonate and R represents an alkyl group having from 1 to 10 carbon atoms optionally substituted by one or more halogen atoms or an aryl group optionally substituted by halogen, alkyl, alkoxy or nitro;

(ii) reacting the resultant sulfonated 4-demethyl-13-dioxolanyl-daunomycinone of formula (4):

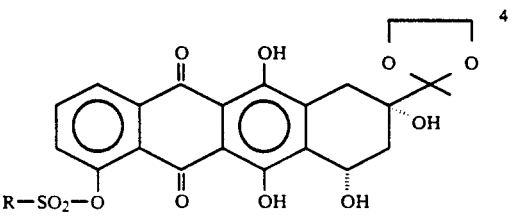
4 wherein R is as defined above, in a reducing environment with a catalytic amount of a compound of formula $$ML_nL'_m \qquad (III)$$

wherein M represents a transition metal atom, L and L', which may be the same or different, each represent an anion or a neutral molecule, and n and m may vary from 0 to 4; and (iii) removing the 13-oxo protecting group from the resultant 4-demethoxy-13-dioxolanyl-daunomycinone (5):

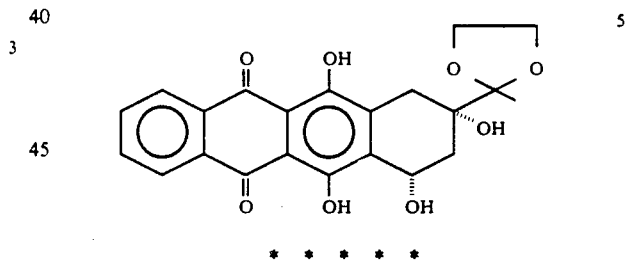
5

* * * * *